US00PP32295P3

(12) United States Plant Patent
Hansen

(10) Patent No.: US PP32,295 P3
(45) Date of Patent: Oct. 6, 2020

(54) ***KNIPHOFIA* PLANT NAMED 'HIGH ROLLER'**

(50) Latin Name: ***Kniphofia* hybrid**
Varietal Denomination: High Roller

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 75 days.

(21) Appl. No.: 16/350,857

(22) Filed: Jan. 24, 2019

(65) Prior Publication Data

US 2020/0245522 P1 Jul. 30, 2020

(51) Int. Cl.
*A01H 5/02* (2018.01)
*A01H 6/56* (2018.01)

(52) U.S. Cl.
USPC ..... Plt./443
CPC ..... *A01H 6/56* (2018.05)

(58) Field of Classification Search
USPC ..... Plt./443
CPC ..... A01H 6/00; A01H 5/02
See application file for complete search history.

*Primary Examiner* — Keith O. Robinson

(57) ABSTRACT

A new and distinct cultivar of Red Hot Poker plant named *Kniphofia* 'High Roller' with long, gracefully-arching, strap-like, keeled, glaucous, gray-green foliage and numerous scapes. Habit is densely growing, winter-hardy, tolerant of heat, deer and rabbits. Numerous scapes of deep coral-orange flower buds that open to near white on tall scapes beginning in the first week of summer and repeating into early August. The new plant is useful for landscaping as a specimen, en masse, or as a long-lasting cut flower.

1 Drawing Sheet

Botanical classification: *Kniphofia* hybrid.
Variety denomination: 'High Roller'.

STATEMENT REGARDING PRIOR DISCLOSURES UNDER 37 CFR 1.77(B)(6)

The first public disclosure of the claimed plant, in the form of a photograph and brief description was on a website operated by Walters Gardens, Inc. on Feb. 1, 2018. After that, on May 21, 2018 the claimed plant was sold by Walters Gardens, Inc., who obtained the plant and all information relating thereto, from the inventor. No plants of *Kniphofia* 'High Roller' have been sold in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to the new and distinct Red Hot Poker, *Kniphofia* 'High Roller' hybridized under the direction of the inventor at a wholesale perennial nursery in Zeeland, Mich., USA on Aug. 16, 2012 and harvested later in the fall of 2012. The new plant was a single seedling selection resulting from a cross of 'Echo Mango' U.S. Plant Pat. No. 21,706 as the female parent or seed parent and 'Sally's Comet' (not patented) as the male parent or pollen parent. The plant passed initial evaluation in the summer of 2014 and was subsequently given the breeder code 12-3-4 prior to naming. *Kniphofia* 'High Roller' has been successfully asexually propagated by division method since 2014 at the same wholesale perennial nursery in Zeeland, Mich. and subsequently by shoot tip tissue culture, and both methods have been found to be stable and produce identical plants that maintain the unique characteristics of the original plant through multiple generations.

SUMMARY OF THE PLANT

*Kniphofia* 'High Roller' differs from its parents as well as all other *Kniphofia* known to the applicant. The most similar known *Kniphofia* cultivars are: the female parent 'Echo Mango', 'Orange Vanilla Popsicle' U.S. Plant Pat. No. 24,292 and 'Red Hot Popsicle' U.S. Plant Pat. No. 24,036. 'Orange Vanilla Popsicle' is much shorter in scape and foliage height with fewer flowers per stem. 'Red Hot Popsicle' is significantly shorter in scape and foliage height with fewer flowers per stem that stay the same reddish color in bud and open flower. 'Sally's Comet' is taller and has flowers that are nearly green in bud and open to bright yellow. 'Echo Mango' has flowers that are more yellowish-orange in bud and yellow in flower color.

*Kniphofia* 'High Roller' differs from these above cultivars and all cultivars known to the inventor in that it has:

1. Gracefully arching, strap-like, keeled, gray-green foliage.
2. Rapidly growing, dense habit, winter-hardy, heat tolerant, rabbit and deer tolerant, large-sized clumps.
3. Numerous spikes of deep coral-orange flower buds that open to near white tepals on tall stems;
4. Flowering beginning the first week of summer and repeating into early August in Michigan.

BRIEF DESCRIPTION OF THE DRAWINGS

The photographs of *Kniphofia* 'High Roller' demonstrate the overall appearance of the plant, including the unique traits. The plants were five-year-old growing in a full-sun trial garden. The colors are as accurate as reasonably possible with color reproductions. Ambient light spectrum, source and direction may cause the appearance of minor variation in color.

DETAILED BOTANICAL DESCRIPTION

Figure 1:
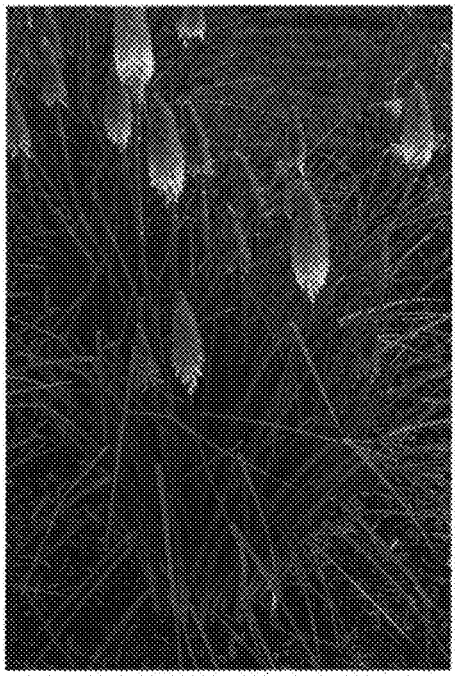
FIG. 1 shows the side-view habit of a five-year-old plant in midseason flowering.
Figure 2:
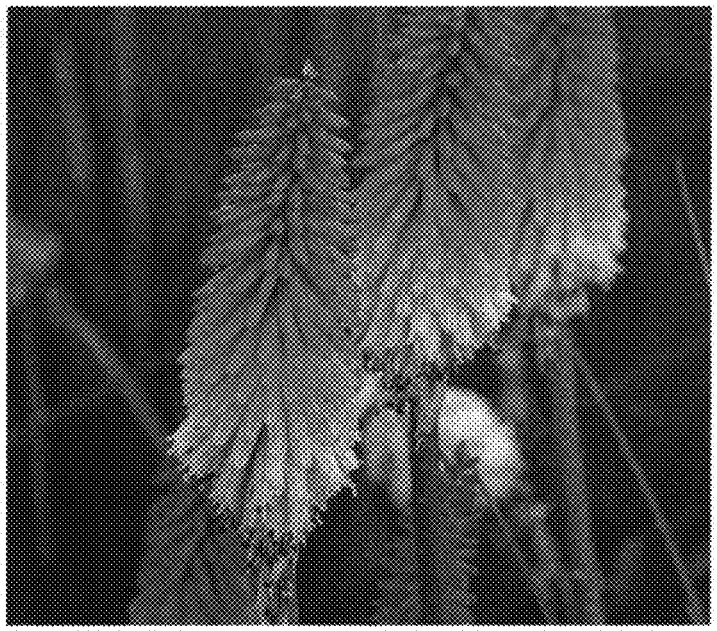
FIG. 2 shows a close-up of the flowers and buds.

The following descriptions and color references are based on the 2015 edition of The Royal Horticultural Society Colour Chart except where common dictionary terms are used. The new plant, *Kniphofia* 'High Roller', has not been observed under all possible environments. The phenotype may vary slightly with different environmental conditions, such as temperature, light, fertility, moisture and maturity levels, but without any change in the genotype. The following observations and size descriptions are of a five-year-old plant in a trial garden of a wholesale perennial nursery in Zeeland, Mich. under full sun with supplemental water and fertilizer as needed.

Botanical classification: *Kniphofia* hybrid;

Parentage: *Kniphofia* 'Echo Mango' as the female or seed parent and 'Sally's Comet' as the male or pollen parent;

Propagation method: By garden division of the rhizome and later shoot tip tissue culture;

Growth rate: Vigorous, flowering in 3.5 liter containers in about 10 to 12 weeks from a tissue culture 25 mm plug liner in late winter to spring and from a one-year-old bare root plant to flowering in 6 to 8 weeks in a 4.0 liter container;

Rooting habit: Fibrous from base of rhizomes, lightly branching; color nearest RHS 158C;

Plant description: Dense, rhizomatous, acaulescent, perennial clump with long thin foliage to about 108.0 cm across and about 97.0 cm tall; flowering to about 114.0 cm tall; about 62 peduncles per plant;

Leaves: Linear; keeled at base, triangular in distal half; arranged about 8 leaves per basal division; apex narrowly acute; base truncate, clasping; margin and keeled abaxial midrib micro-dentate; no fragrance observed;

Leaf size: To about 99.0 cm long and 25.0 mm across at base, average about 87.0 cm long and 20.0 mm across at base;

Leaf color: Young base nearest RHS NN155A both abaxial and adaxial, distally between RHS 144A and RHS 138A both abaxial and adaxial; mature both surfaces between RHS 144A and RHS 138A;

Leaf venation: Parallel; color same as leaf abaxial and adaxial, between RHS 144A and RHS 138A;

Stem: Acaulescent; rhizome about 18.0 mm across at base;

Inflorescence: In spike-like raceme; terete; about 300 flowers per stem; flowering portion to about 34.0 cm tall and about 7.0 cm across; lasting about three weeks; flower spacing less than 1.0 mm apart on raceme in distal region and about 2.5 cm in lowest flowers;

Peduncle: Terete; glabrous; glaucous; solid, not fistulose; to about 114.0 cm long and 9.0 mm diameter; average 102.0 cm tall and 8.5 mm diameter; flowering in distal 34.0 cm;

Peduncle color: Nearest RHS 146D;

Buds one day prior to anthesis: Ellipsoidal to tubular with swollen subacute apex and rounded base; glabrous; lustrous; about 24.0 mm long and about 3.5 mm diameter at base and 5.0 mm diameter at widest point near apex;

Bud attitude: Beginning outwardly and drooping as maturing toward anthesis;

Bud color on day prior to anthesis: Abaxial distal and dorsal portions RHS 155A with ventral midrib nearest RHS 169D and dorsal midrib nearest RHS 171B;

Buds five days prior to anthesis: Shape size 17.0 mm long, 3.5 mm diameter in middle and 2.5 mm diameter at base; color between RHS 178C and RHS 145A on ventral tepals and between RHS 167D and RHS 165A on dorsal tepals;

Flowers: Terete; six tepals forming tubular corolla; perfect; actinomorphic; individually open and effective about three to four days;

Corolla size: To about 23.5 mm long, fused in basal about 19.0 mm; face to about 7.0 mm tall and about 7.0 mm wide; tube about 3.5 mm diameter near base and about 5.0 mm near throat;

Flower attitude: Drooping;

Flower fragrance: None detected;

Flowering period: Individual racemes effective for about 3 weeks; beginning in early summer Michigan for about six week, then continuing with repeat racemes until early fall with a short two week break in the heat of the summer;

Tepals: Six, in two identical sets of three; both sets with acute apices and fused in basal 19.0 mm forming a long tube, and divided in distal 4.5 mm; margin entire; glabrous and lustrous abaxial and adaxial; about 23.5 mm long and about 3.0 mm across just above fusion point;

Tepal color (young abaxial): Nearest RHS 8A; (young adaxial): between RHS 165C and RHS 160B with midrib nearest 155B;

Tepal color (mature abaxial): Nearest RHS 155C with midribs nearest RHS 150C; (mature adaxial): nearest RHS NN155D with midrib nearest 150C;

Androecium: Six; variable lengths, with filament lengths between 24.0 mm and 29.0 mm;

*Filaments*.—Six; exserted; terete; glabrous; lustrous; from about 24.0 to 29.0 mm long and about 0.5 mm diameter; color nearest RHS NN155B.

*Anther*.—Slightly flattened ellipsoidal; flattened ventrally to dorsally; about 2.0 mm long and 1.5 mm across and 1.0 mm thick; dorsifixed; longitudinal; color nearest RHS 13B.

*Pollen*.—Abundant: color nearest RHS 11C.

Gynoecium: single; about 26.0 mm long;

*Style*.—Terete; glabrous; lustrous; about 23.0 mm long and 0.7 mm diameter: color more white than RHS 23D.

*Stigma*.—Flattened, round; about 0.3 mm across; color nearest RHS NN155A.

*Ovary*.—Superior; globose; acute apex, rounded base; about 2.5 mm long and 2.5 mm diameter; color nearest RHS 146C.

Pedicel: Cylindrical; glabrous; lustrous; stiff; drooping; about 1.7 mm long and about 0.5 mm diameter;

Pedicel color: One day prior to opening nearest RHS 178B, one day prior to opening nearest RHS 173C, four days after opening nearest RHS 146D;

Bracts: Hyaline; lanceolate; at cauline nodes and subtending individual flowers; with acute apices and truncate base; to about 5.0 mm long and 2.0 mm across at base; decreasing distally; average about 4.0 mm long and 1.5 mm across; color blushed with nearest RHS 161D;

Fruit: Tri-valved loculicidal capsule; globose; about 7.0 mm long and 6.0 mm diameter; glabrous; with rounded apex and rounded base; typically six to nine seeded; color upon maturity nearest RHS 200A;

Seed: Irregular with angular sides, acute apex and base; about 3.5 mm long and 2.5 mm across; color nearest RHS 200A;

Disease and pest resistance: 'High Roller' shows limited susceptibility to rust. There are many genera of pathogenic rust, but the specific identification of the slight rust found on the new plant has not been identified and is not known by the inventor. Resistance beyond that of other *Kniphofia* has not been observed. The plant grows best with good drainage and is able to tolerate some heat when established. Hardiness at least from USDA zone 6 through 9 and 5b with protection.

I claim:

1. A new and distinct cultivar of Red Hot Poker plant named *Kniphofia* 'High Roller' as herein described and illustrated.

* * * * *